US009848890B2

(12) United States Patent
Yoon et al.

(10) Patent No.: US 9,848,890 B2
(45) Date of Patent: Dec. 26, 2017

(54) DEVICES AND METHODS FOR THE PREPARATION OF INTERVERTEBRAL DISCS

(75) Inventors: Samuel Yoon, Wyndmoor, PA (US); Sean Suh, Bensalem, PA (US); Robert Leonard, Furlong, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 260 days.

(21) Appl. No.: 13/183,803

(22) Filed: Jul. 15, 2011

(65) Prior Publication Data
US 2013/0018376 A1     Jan. 17, 2013

(51) Int. Cl.
| | | |
|---|---|---|
| *A61B 17/00* | (2006.01) | |
| *A61B 17/16* | (2006.01) | |
| *A61B 17/32* | (2006.01) | |
| *A61B 17/3207* | (2006.01) | |
| *A61B 17/02* | (2006.01) | |

(52) U.S. Cl.
CPC ...... *A61B 17/1617* (2013.01); *A61B 17/1642* (2013.01); *A61B 17/1671* (2013.01); *A61B 17/32002* (2013.01); *A61B 17/320725* (2013.01); *A61B 17/1628* (2013.01); *A61B 17/1659* (2013.01); *A61B 2017/00261* (2013.01); *A61B 2017/0256* (2013.01); *A61B 2017/320733* (2013.01)

(58) Field of Classification Search
CPC .......... A61B 17/1617; A61B 17/32002; A61B 17/1642; A61B 17/16; A61B 17/1613; A61B 17/1615; A61B 17/320725

USPC ................ 606/79–85, 86 R, 92–94
See application file for complete search history.

(56) References Cited

U.S. PATENT DOCUMENTS

| | | | |
|---|---|---|---|
| 5,591,170 A * | 1/1997 | Spievack ............. | A61B 17/151 30/122 |
| 6,740,090 B1 * | 5/2004 | Cragg et al. .................... | 606/79 |
| 2003/0130664 A1 * | 7/2003 | Boucher ............ | A61B 17/1631 606/86 R |
| 2008/0065020 A1 * | 3/2008 | Ralph et al. ............. | 604/164.11 |
| 2008/0114364 A1 * | 5/2008 | Goldin ............... | A61B 17/1617 606/79 |
| 2010/0114098 A1 * | 5/2010 | Carl ............................... | 606/80 |

\* cited by examiner

*Primary Examiner* — Si Ming Ku

(57) ABSTRACT

A power tool for removing an intervertebral disc and preparing vertebral endplates is described. The power tool may include a cutting element, and the height of the cutting element may be adjustable. The cutting element may be a braided cable and may include one or more beads to enhance the effectiveness of the cable. The cutting element may have a minimum height requirement, which may not be satisfied in patients with a collapsed disc due to degenerative disc disorder. For these patients, also described are bone tamps for increasing the intervertebral distance and providing access to tissues distal to the tamp. One type of bone tamp features an inflatable balloon with an inner lumen. Another type of bone tamp includes an expanding distal end and an inner cannula. Also described is a manual expander scraper tool that is compatible with both types of bone tamp.

16 Claims, 11 Drawing Sheets

DEVICES AND METHODS FOR THE PREPARATION OF INTERVERTEBRAL DISCS

BACKGROUND OF THE DISCLOSURE

1. Field of the Disclosure

The disclosure is directed to devices and methods for the preparation of one or more intervertebral discs as part of a surgical procedure to treat, for example, damage to the discs.

2. Related Art

A "discectomy" procedure removes the nucleus pulposus from an intervertebral disc to relieve pain and/or prepare the vertebrae for a fusion procedure. Many tools exist for performing this procedure, but most of these are manual tools. Moreover, fewer than 5% of discectomies are performed with power tools. The use of power tools may speed the procedure, thereby reducing injury to surrounding tissues and shortening the post-operative recovery period.

Arthroscopic shavers have been used for discectomies, but they are prone to clogging and are unable to properly prepare vertebral endplates for fusion. RF energy devices have been developed but are relatively slow and can burn tissue. High pressure water jet devices have been developed, but they require a cumbersome and expensive external pump for operation. Battery powered auger devices for removing 2 cc of nucleus material are available, but they cannot remove enough material for fusion procedure. Accordingly, there is a need for a tool that does not clog and removes a sufficient amount of material.

Similarly, the use of any power tool may be hampered when working on a disc that has collapsed due to, e.g., disc herniation or degenerative disc disease. When the disc has collapsed, the adjacent vertebrae are closer together and may not provide the minimum height needed to operate a power tool. Inflatable bone tamps are available to increase the space between the vertebrae, but existing tamps are not compatible with power tools. In particular, inflatable tamps block or restrict access to disc material that is immediately distal to the tamp's balloon, as well as other areas. Accordingly, there is a need for a bone tamp that is compatible with power tools used to perform a discectomy.

SUMMARY OF THE DISCLOSURE

The disclosure meets the foregoing need and allows surgeons to perform a discectomy using power tools and an inflatable bone tamp, which may result in a significantly faster operation and other advantages apparent from the discussion herein.

Accordingly, one aspect of the disclosure describes a device for the removal of a whole or partial intervertebral disc. The device includes a handle and an outer sheath connected to the handle. The device also includes an inner core connected to the handle and extending through the outer sheath. The inner core includes a flexible cutting element located past the distal end of the outer sheath. The device further includes a motor that rotates the inner core, as well as a control that adjusts or alters the height of the flexible cutting element.

The device may optionally include an outer core connected to the inner core and located between the inner core and the outer sheath. The outer core includes an auger portion located between the flexible cutting element and the distal end of the outer sheath. The outer core may be rotated by the motor or the inner core. The flexible cutting element may include a metal, a superelastic metal, or a polymer. The flexible cutting element may be a braided cable, a linked chain, a dual blade, or a flexible member. The braided cable may include one or more beads. The control may be a trigger that is squeezed by a user of the device to adjust the height of the cutting element. The device may also include one or more batteries to power the motor. The flexible cutting element may have a height between about 0 mm and about 20 mm. More specifically, the cutting element may have a height between about 4 mm and about 16 mm.

According to another aspect of the disclosure, a device for separating two vertebrae that are in closer proximity due to degenerative disc disorder includes a balloon that may be inserted between the vertebrae. The balloon has a compressed state, an expanded state, a distal end, and a proximal end. The proximal end of the balloon is connected to the distal end of a central shaft, and the two component are in fluid communication. An inflation port is in fluid communication with the central shaft and may transport fluid to inflate the balloon, putting it in an expanded state, or to deflate the balloon, putting it in a compressed state. The device further includes an inner lumen located within the central shaft but sealed against fluid communication with the shaft, the balloon, and the inflation port. The inner lumen passes through the balloon to a distal port on the distal end of the balloon. A lumen port is located at the proximal end of the central shaft. The lumen port, the inner lumen, and the distal port define a linear path from the lumen port and the proximal end of the central shaft to the distal port and the distal end of the balloon.

The fluid used to inflate and deflate the balloon may be air, saline, and/or nitrogen gas.

In yet another aspect of the disclosure, a device for separating two vertebrae that are in closer proximity due to degenerative disc disorder includes an outer tube and an inner cannula located within the outer tube. The inner cannula has an outer diameter that is smaller than the inner diameter of the outer tube. The distal end of the outer tube includes two or more axial cuts, two or more circumferential cuts, and a narrowed inner diameter that is smaller than the outer diameter of the inner cannula. The distal end of the outer tube is configured to expand radially when the cannula is advanced into the distal end of the outer tube.

The inner cannula may advance into the distal end by means of a threaded interface.

In a further aspect of the disclosure, a device for the removal of bone or tissue includes a handle and an outer shaft connected to the handle. The outer shaft includes a rounded tip distal to the handle and a window on one side of the shaft near the tip. The device also includes an inner core located in to outer shaft and connected to the handle. The inner core includes a curved tip that may cut through bone or tissue. The device further includes a control knob connected to the handle and the outer shaft. The control knob slides the outer shaft relative to the inner core, thereby extending or retracting the curved tip through the window in the outer shaft.

The outer shaft of the device may be configured to be rotationally stationary relative to the handle. The handle may be a T-handle. The inner core may include a superelastic metal, and the superelastic metal may be nitinol. The curved tip may include a sharp point and sharp edges configured to through bone or tissue.

Additional features, advantages, and aspects of the disclosure may be set forth or apparent from consideration of the following detailed description, drawings, and claims. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate aspects of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

DETAILED DESCRIPTION OF THE DISCLOSURE

Figure 1:
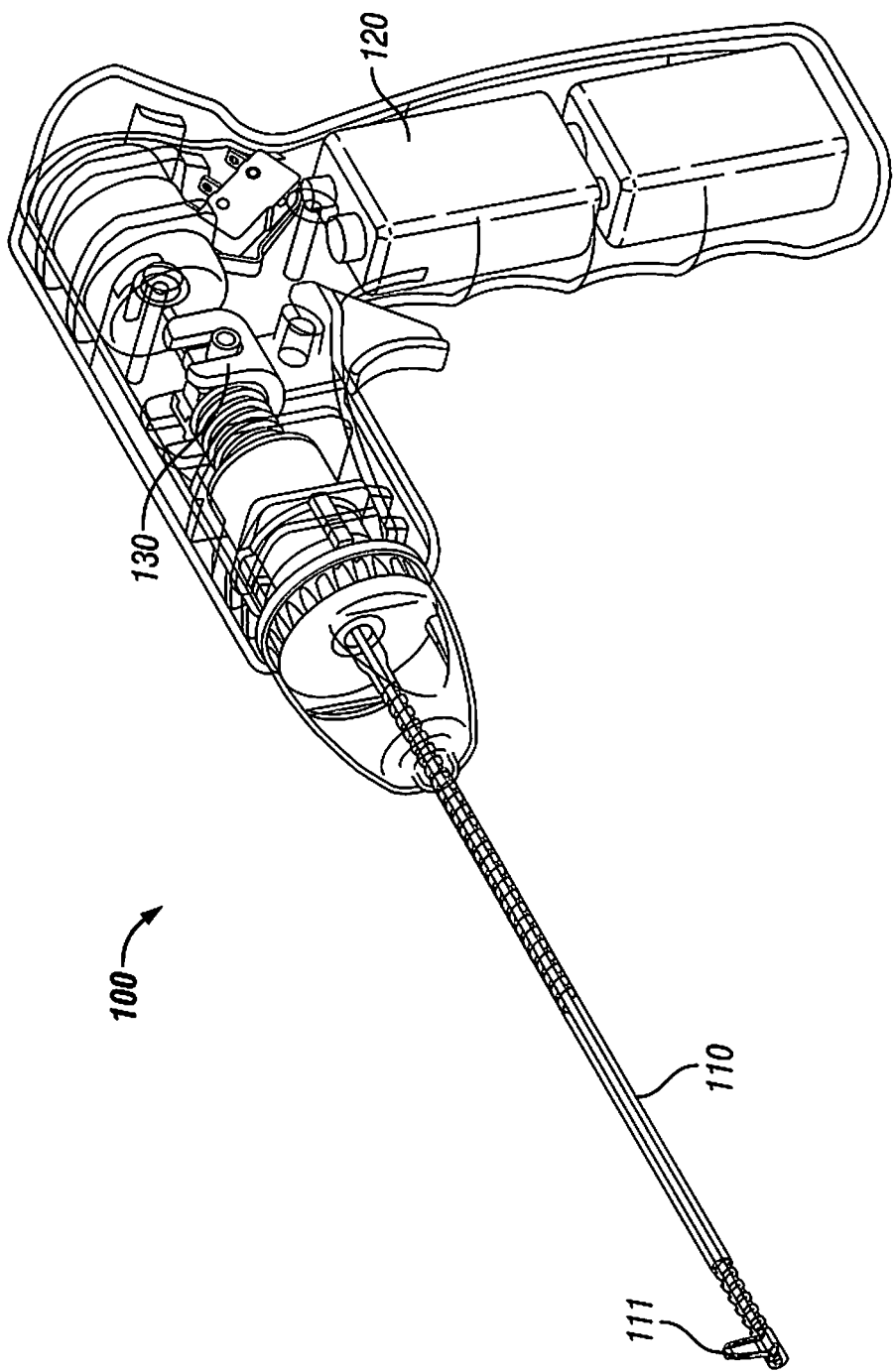
FIG. 1 shows a power tool for use in discectomies, according to an aspect of the disclosure.

The aspects of the disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one embodiment may be employed with other aspects as the skilled artisan would recognize, even if not explicitly stated herein. Descriptions of well-known components and processing techniques may be omitted so as to not unnecessarily obscure the aspects of the disclosure. The examples used herein are intended merely to facilitate an understanding of ways in which the disclosure may be practiced and to further enable those of skill in the art to practice the aspects of the disclosure. Accordingly, the examples and aspects herein should not be construed as limiting the scope of the disclosure, which is defined solely by the appended claims and applicable law. Moreover, it is noted that like reference numerals represent similar parts throughout the several views of the drawings.

An intervertebral disc is located between each pair of vertebrae in the spine, except between the first and second cervical vertebrae. The discs act as joints, allowing some degree of rotation between adjacent vertebrae. The discs also function as shock absorbers, cushioning the spine against jostling and impacts.

Each disc is made of two main components. An outer layer of fibrocartilage, called the annulus fibrosus, that surrounds the inner matrix, the nucleus pulposus. The fibers of the annulus fibrosus contain the nucleus pulposus and distribute pressure across the disc. The nucleus pulposus has a jelly-like consistency and acts as the main shock absorber in the disc.

As people age, the nucleus pulposus gradually dehydrates, degrading its ability to absorb shock and stresses to the spine. These stresses are instead transferred to the annulus fibrosus, which can cause structural degradation. Dehydration of the nucleus pulposus and damage to the annulus fibrosus can cause pain, which can be severe and debilitating in some patients. This condition is known as degenerative disc disorder (DDD).

The annulus fibrosus can be torn due to injury or trauma, and it is more likely to be torn as a result of changes due to the natural aging process. When the annulus is torn, the nucleus pulposus may extrude through the tear. This condition is commonly referred to as a herniated disc, although it may also be known as a prolapsed disc, ruptured disc, or slipped disc. The herniated disc can press against nerves, causing severe pain, numbness, tingling, and decreased strength or range of motion. A herniated disc can also cause pain when the nucleus pulposus, which contains inflammatory chemicals, directly contacts nerves.

Both degenerative disc disease and herniated discs may be treated with a discectomy, the removal of the affected disc. A discectomy may be performed either as a stand-alone procedure or in conjunction with a spinal fusion. Discectomies and spinal fusions may also be used to treat other conditions, including back pain, spinal tumors, and vertebral fractures.

Traditionally, discectomies are performed as open surgical procedures. Muscles and ligaments surrounding the spine are carefully cut and peeled away until the surgeon can access the vertebrae directly. The damaged or diseased disc is removed with specialized hand tools. This procedure is lengthy, and the damage to the surrounding tissues is magnified by the time spent on the operating table.

More recently, minimally invasive surgery (MIS) techniques have been developed to permit surgery without as much disruption to the surrounding and supporting tissues. However, these procedure are still typically performed with hand tools. The injury to the patient could be further reduced by performing the procedure more quickly. Power tools have been developed to quickly remove the disc material. However, existing power tools suffer from one or more defects or shortcomings, including an insufficient cutting height, insufficient removal of disc material, and clogging.

According to one aspect of the disclosure, a rotary power tool 100 may incorporate a variable height cutting element 111. The power tool 100 may be capable of rapidly removing disc material, especially the nucleus pulposus, and preparing vertebral endplates for a spinal fusion procedure. The variable height of the cutting element 111 can accommodate varying geometries and distances between vertebrae, which may result in cleaner and more thorough removal and preparation. In addition, the variable height cutting element 111 may pass through the inner lumen of an inflatable bone tamp, such as the one described below.

FIG. 1 shows a power tool 100 for use in discectomies, according to an aspect of the disclosure. The power tool 100 may include a shaft 110, a handle 120, and a body 130. A cutting element 111 may be located at the distal end of the shaft 110.

Figure 2:
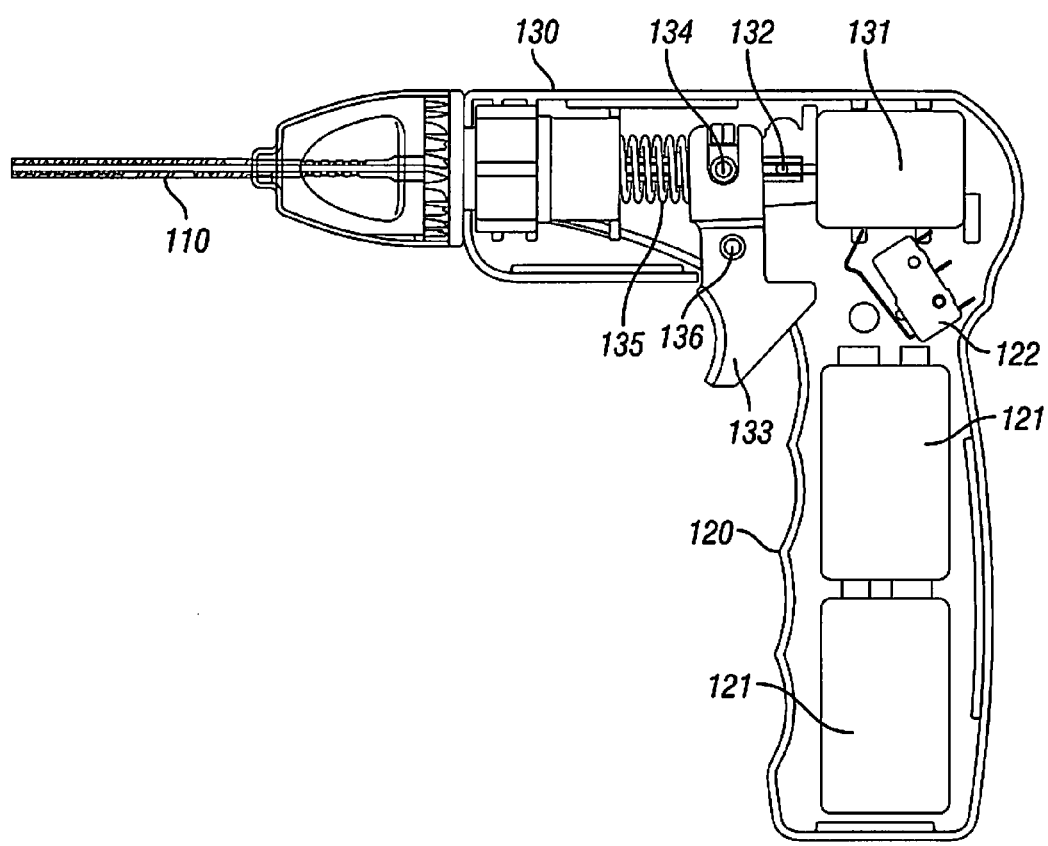
FIG. 2 shows the interior components of the power tool of FIG. 1.

FIG. 2 shows the interior components of the power tool 100. One or more batteries 121 may be located in the power tool, for example handle 120. The batteries may be of any type and/or number sufficient to provide required power to the components of the power tool 100, as will be understood by one having ordinary skill in the art. A switch 122 may be located in the handle and may control operation of the power tool 100.

The body 130 may include a control for controlling the height of cutting element 111. As shown in FIG. 2, the control may be a trigger-type apparatus 133, although the control may be implemented with different configurations without departing from the spirit and scope of the disclosure and/or claims, as will be understood by one having ordinary skill in the art. During operation, a user of the power tool 100 may squeeze the trigger 133, causing it to rotate about pivot 136. The rotation of the trigger 133 may push plunger 134 in the direction of the shaft 110. Plunger 134 may be connected to one or more components of the shaft, including the inner core 115 (see FIG. 3). As plunger 134 moves with respect to shaft 110, it may lengthen the inner core 115 in comparison to the overall length of the shaft 110. This relative increase in length may in turn increase the height of the cutting element 111, as described in detail below with respect to FIG. 3. In certain aspects of the disclosure, the cutting element 111 may be adjustable in height between 0 mm and 20 mm. In further aspects of the disclosure, the cutting element 111 may be adjustable in height between 4 mm and 16 mm.

A motor 131 may be located in the body 130 just above the handle 120, and the motor may function to rotate one or more components of the shaft 110, as described in detail below with respect to FIG. 3. A spring 135 may press plunger 134 thereby acting to decrease the height of cutting element 111 in the absence of pressure on the trigger 133. Connector 132 may connect plunger 134 to the motor 131. In addition, connector 132 may allow the distance between the plunger 134 and the motor 131 to vary, such as when the trigger is squeezed, without disengaging plunger 134 from motor 131.

Figure 3:
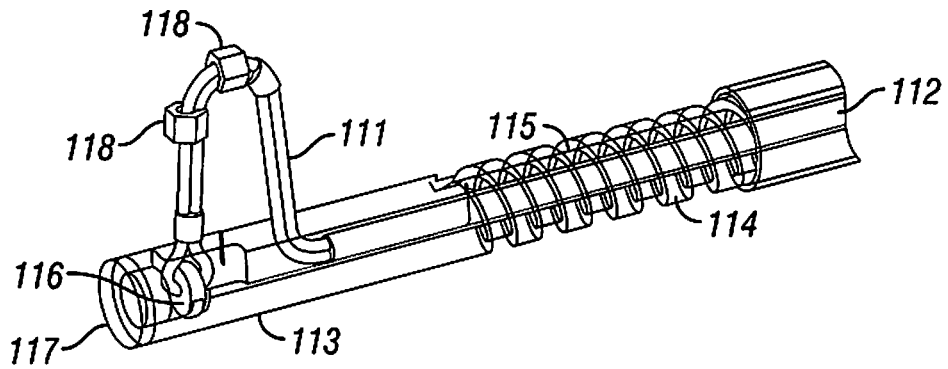
FIG. 3 shows the distal end of the shaft of the power tool of FIG. 1.

FIG. 3 shows the distal end of shaft 110. The shaft 110 may include an outer sheath 112. The outer sheath 112 may be connected to body 130 and may not rotate. In contrast, inner core 115 may be connected to plunger 134 and may be rotated by motor 131. Inner core 115 may include a cutting element 111. When the trigger is squeezed and the inner core 115 increases in length relative to shaft 110, the extra length is taken up by the cutting element 111, which increases in height. As shown in FIG. 3, the cutting element may be a braided cable, and the braided cable may be fitted with one or more beads 118 to enhance the effectiveness of the cutting element 111.

Shaft 110 may also include an outer core 113. The outer core 113 may provide an auger 114 to aid in the removal of tissue and bone material that has been cut by the cutting element 111. Outer core 113 may rotate by a mechanical linkage to the inner core 115 or other arrangement as will be understood by one having ordinary skill in the art. Cutting element 111 may be attached to a ring 116, which may provide some stability to the cutting element. Shaft 110 may also have a smooth, rounded distal end 117.

Figure 4A:
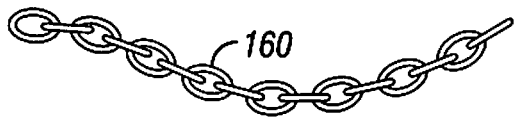
FIGS. 4A, 4B, and 4C show alternate constructions that may be used to form the cutting element of the power tool of FIG. 1.
Figure 4B:
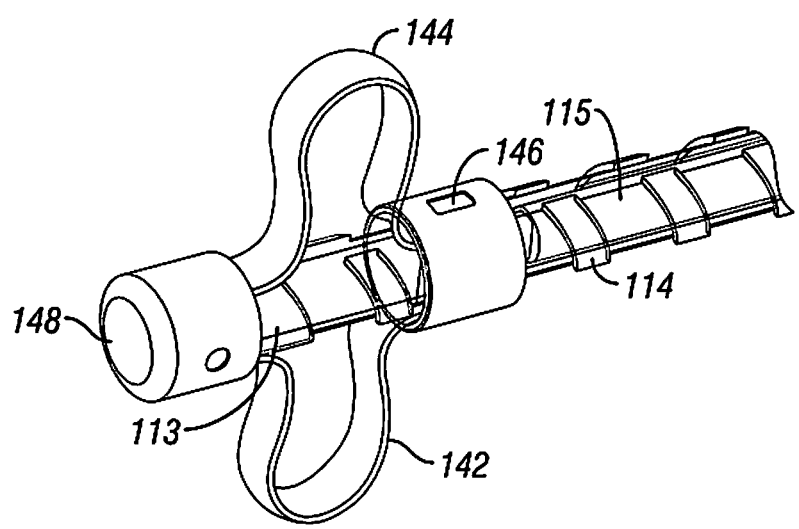
Figure 4C:
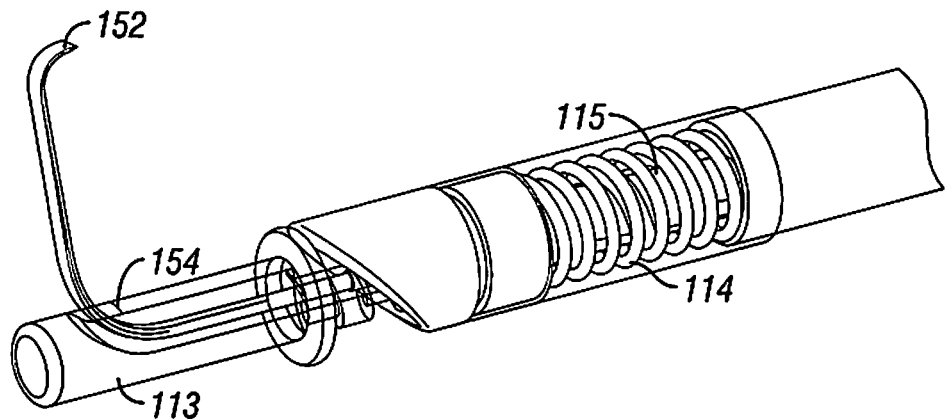

FIGS. 4A, 4B, and 4C show alternate materials and constructions that may be used to form the cutting element 111 in place of the braided cable discussed above. FIG. 4A shows a linked chain 160 that may be arranged in a manner similar to cutting element 111. The linked chain 160 may be arranged in outer core 113. FIG. 4B shows a dual blade having blades 142, 144 that are held by a cap 148 and ring 146, movement of the ring 146 relative to the cap 148 extends blades 142, 148, movement may be caused by a connection of the cap 148/ring 146 to the push plunger 134 to move each relative to one another. FIG. 4C shows a flexible member 152 that moves out of a window 154 through actuation of push plunger 134 to change the relative position of the flexible member 152 to outer core 163. Additional implementations of the cutting element 111 are contemplated and are within the spirit and scope of the disclosure and claims. The cutting element, in any implementation or embodiment, may be made from any appropriate material, including, e.g., metal, superelastic metal, and polymer.

Figure 5:
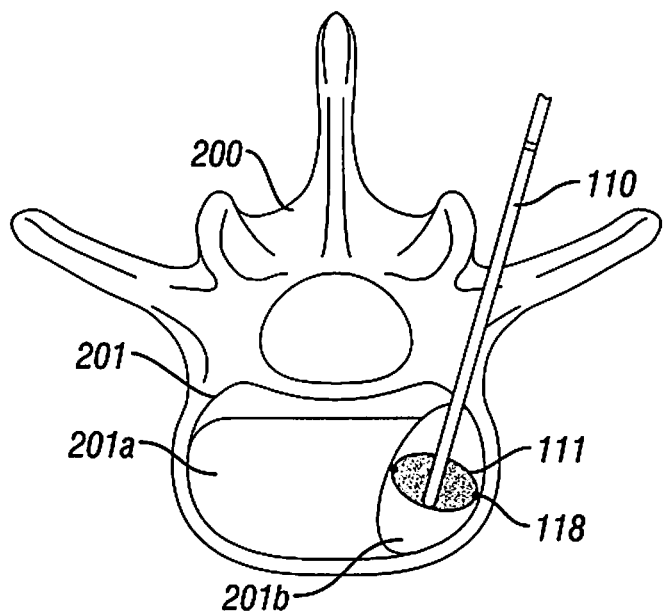
FIG. 5 illustrates a power tool in use on a vertebra and an intervertebral disc.

FIG. 5 illustrates the power tool 100 in use on a vertebra 200 and an intervertebral disc 201. The disc 201 is divided into two zones: zone 201b may be reachable with the shaft 110 in a straight configuration. Zone 201a may be unreachable with a straight tool. In some aspects of the disclosure, the inner core and outer core may be made of flexible materials to permit axial articulation, as well as axial rotation. This type of articulating instrument may be able to remove material from zone 201a.

Performing a discectomy is difficult when a disc has collapsed or compressed due to degenerative disc disease. Collapsed discs present an additional obstacle for power tools, such as power tool 100, because the tool may require a minimum height for its cutting element to operate properly. Traditionally, collapsed discs can be ameliorated somewhat during surgery by the use of inflatable or expanding bone tamps, which are inserted between the vertebrae and then push them apart. These bone tamps, however, may block a power tool from reaching much of the disc, thus negating the advantages of power tools.

One solution is to use a bone tamp that provides a passage for the power tool through the tamp's expansion apparatus. An example of such a tamp may be seen in FIGS. 6-9, which illustrate an exemplary inflatable bone tamp with a through lumen, according to aspects of the disclosure.

Figure 6:
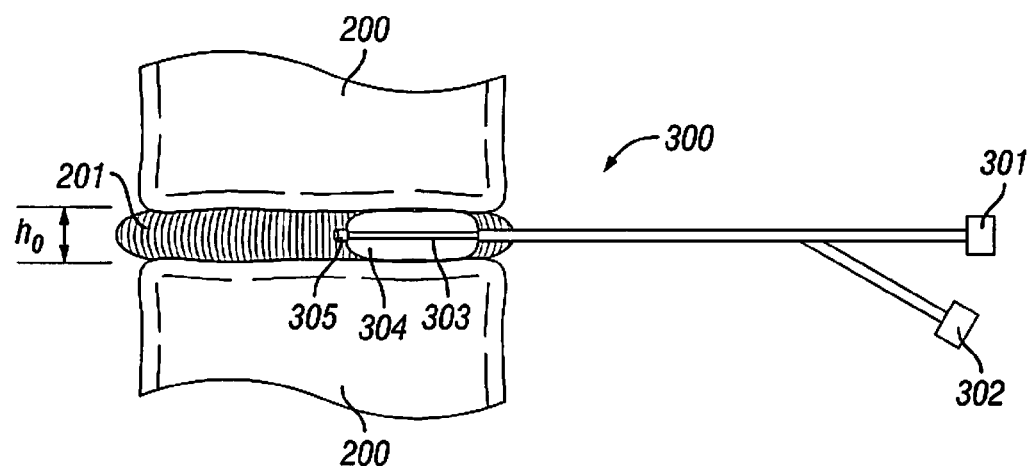
FIG. 6 shows the first stage of using an inflatable bone tamp with through lumen in a discectomy.

FIG. 6 shows the first stage of using an inflatable bone tamp with through lumen in a discectomy. The bone tamp 300 may be inserted between two vertebrae 200 where the intervertebral disc 201 has collapsed. While the bone tamp 300 is shown inserted between the vertebral bodies, the tamp 300 may also or alternatively be inserted between the processes, pedicles, or laminae of the vertebrae. The tamp 300 may include a balloon 304, which is deflated at this stage, and a lumen 303 that passes through the balloon 304. The lumen 303 may be straight and connected to a lumen port 301 at the proximal end of the bone tamp 300 and to a distal port 305 at the distal end of the tamp 300. The bone tamp 300 may also include an inflation port 302 for providing a gas or liquid under pressure to the balloon 304.

Figure 7:
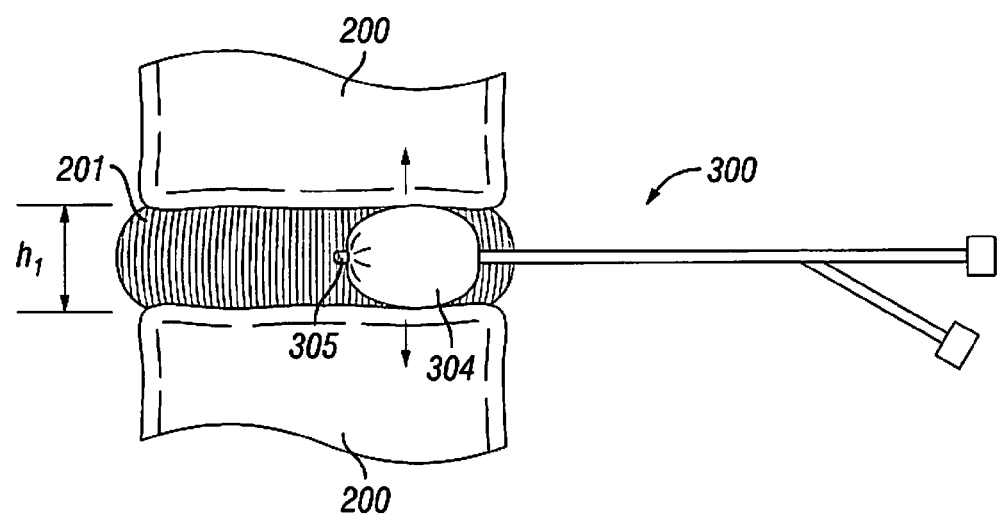
FIG. 7 shows the bone tamp of FIG. 6 in an inflated configuration.

FIG. 7 shows the bone tamp 300 in an inflated configuration. As the balloon 304 is inflated, it pushes the vertebrae 200 apart, as indicated by the arrows. Any appropriate gas or liquid may be used to inflate the balloon 304, including, e.g., saline, air, and nitrogen.

Figure 8:
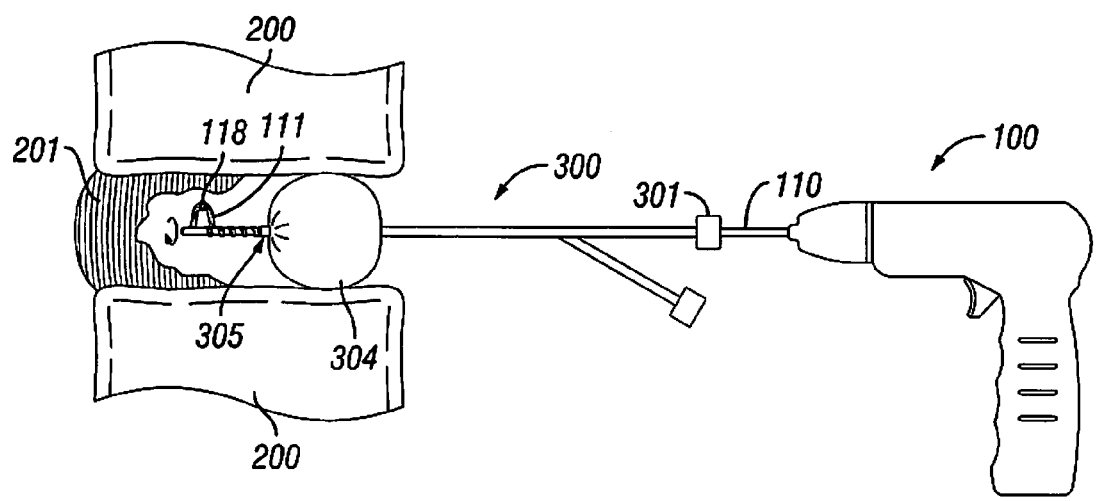
FIG. 8 shows the inflated bone tamp of FIG. 6 holding vertebrae apart while a power tool is used to remove an intervertebral disc.

FIG. 8 shows the inflated bone tamp 300 holding vertebrae 200 apart while power tool 100 is used to remove the intervertebral disc 201. The shaft 110 of power tool 100 may be inserted into the lumen port 301 of the bone tamp 300. The lumen 303 passes through the balloon 304 and connects to distal port 305. The inflated balloon 304 provides at least the minimum clearance between vertebrae 200 for power tool 100 to be used. In particular, the balloon 304 provides sufficient space between the vertebrae for cutting element 111 to rotate and remove soft tissue. The cutting element 111 may optionally include one or more beads 118 to assist in the removal of soft tissue. A surgeon or operator may monitor the removal of tissue and the overall discectomy using arthroscopic or endoscopic techniques or any other appropriate means, as will be understood by one skilled in the art of minimally invasive surgery.

Figure 9:
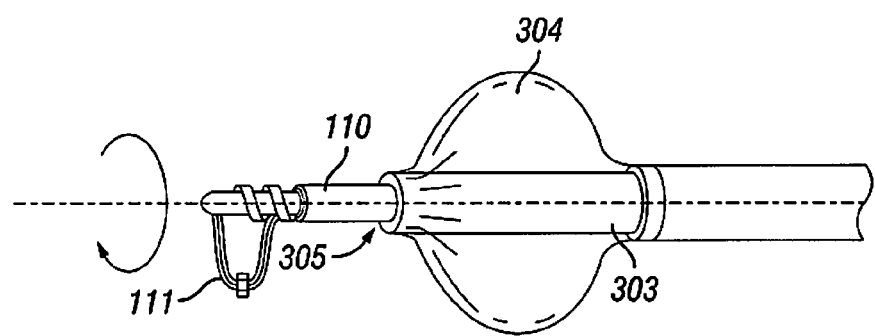
FIG. 9 shows a detail view of the distal end of the bone tamp of FIG. 6 and the shaft of the power tool.

FIG. 9 shows a detail view of the distal end of the bone tamp 300 and the shaft 110 of the power tool 100. Lumen 303 passes through the middle of balloon 304 without affecting the seal or integrity of the balloon. Thus, the balloon 304 will remain inflated even when an instrument is passed through the lumen, and the instrument or tool is able to access tissues and areas that are distal to the balloon 304 and bone tamp 300. The tool illustrated in FIG. 9 may be power tool 100, although many other types of tools may be passed through the lumen. Once the shaft 110 of the tool exits the distal port 305, it is able to turn or rotate freely, and cutting element 111 may begin, for example, to remove the soft tissue of the intervertebral disc. The balloon 304 may provide the minimal height for the cutting element 111 to operate. If the vertebrae 200 are further apart, the surgeon or operator may adjust the height of the cutting element 111, as described above with respect to the power tool 100.

Figure 10:
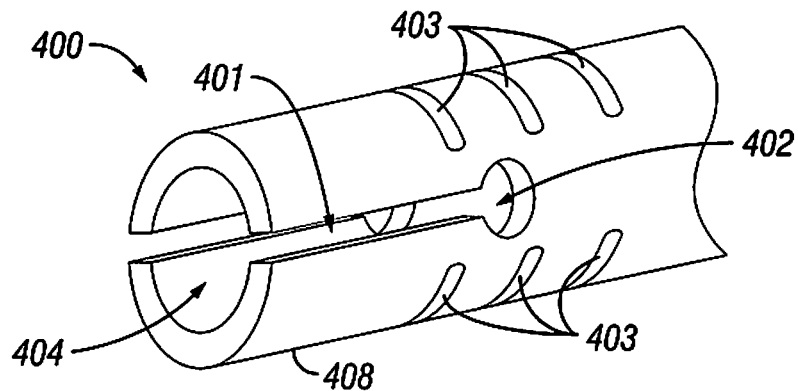
FIG. 10 shows the distal end of an expanding bone tamp, according to an aspect of the disclosure.

FIG. 10 shows the distal end of an expanding bone tamp, according to an aspect of the disclosure. As an alternative to the inflatable bone tamp, a surgeon may wish to use an expanding bone tamp 400 instead. Expansion of the bone tamp 400 is made possible by the design of its distal end, an example of which is shown in FIG. 10. The distal end may include a pair of axial cuts 401 on opposite sides of the outer tube 408. The proximal end of the axial cuts may be formed into an enlarged opening 402. The distal end may also include one or more circumferential cuts 403, as well as a distal opening 404.

Figure 11A:
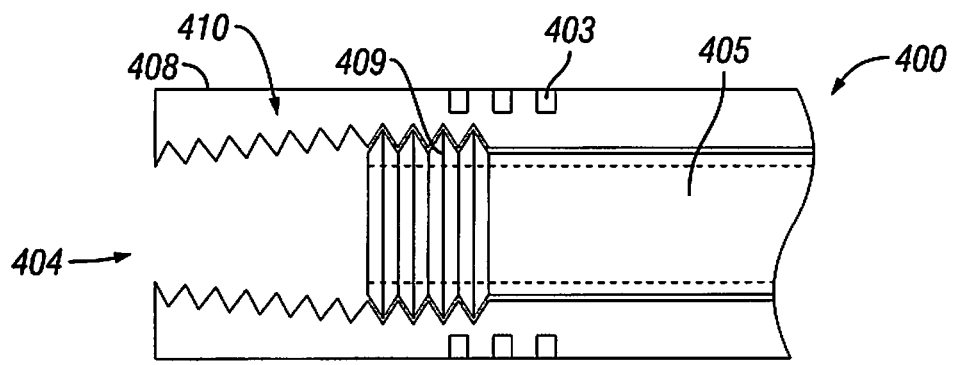
FIG. 11A shows a cross section of the distal end of an expanding bone tamp of FIG. 10 in the collapsed configuration.
Figure 11B:
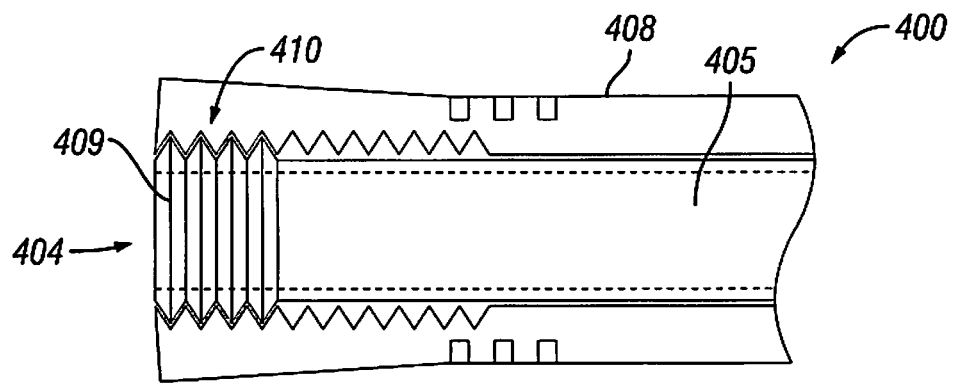
FIG. 11B shows a cross section of the distal end of an expanding bone tamp of FIG. 10 in the expanded configuration.

FIG. 11A shows the interior of the distal end of the bone tamp 400, including an inner cannula 405 and a threaded interface between the cannula 405 and the outer tube 408. The threaded interface may include female threads 410 on the interior of the outer tube 408 and male threads 409 on the exterior of the cannula 405. The threads 410 and 409 may be structured and arranged such that rotating cannula 405 relative to outer tube 408 may draw the cannula along the outer tube 408. Rotation in one direction may bring the distal port 406 of the cannula 405 closer to the distal opening 404 of the outer tube 408, while rotation in the opposite direction may increase the distance between the distal port 406 and the distal opening 404. As outer tube 408 may have a narrowed inner diameter in its distal end, bringing the distal ends of the tube 408 and the cannula 405 closer together may result in expansion of the distal end of the outer tube 408, as described below with respect to FIGS. 12A-14B.

Figure 12A:
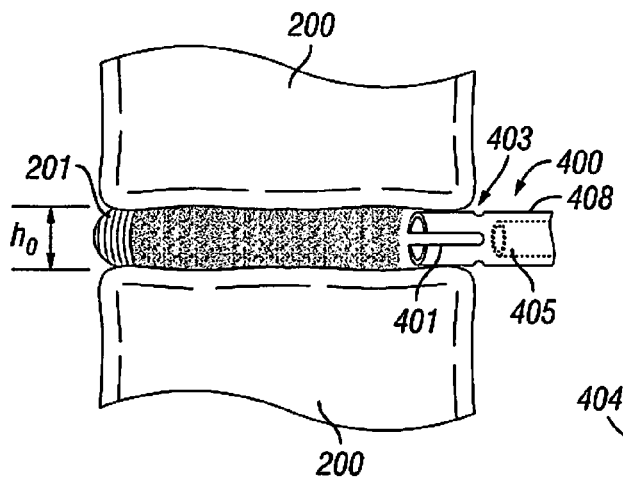
FIG. 12A shows the expanding bone tamp of FIG. 10 after it has been inserted between two vertebrae surrounding a collapsed disc.
Figure 12B:
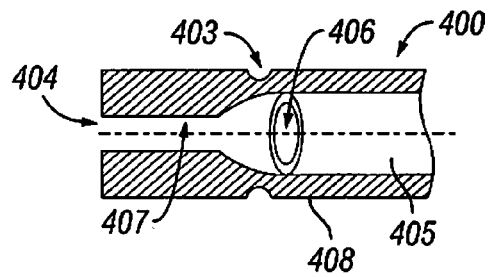
FIG. 12B shows a detail cross section view of the bone tamp 400 from FIG. 11A.

FIG. 12A shows the expanding bone tamp 400 after it has been inserted between two vertebrae 200 surrounding a collapsed disc 201, and FIG. 12B shows a detail view of the bone tamp 400 from FIG. 12A. While the bone tamp 400 is shown inserted between the vertebral bodies, the tamp may also or alternatively be inserted between the processes, pedicles, or laminae of the vertebrae. The bone tamp 400 may include an outer tube 408 and an inner cannula 405. Internally, the distal end of the outer tube 408 may include a narrowed inner diameter 407. The inner cannula 405 may be disposed within the outer tube 408, and the width of the cannula 405 may be wider than the narrowed inner diameter 407 of the outer tube 408. The cannula 405 may include a distal port 406.

Figure 13A:
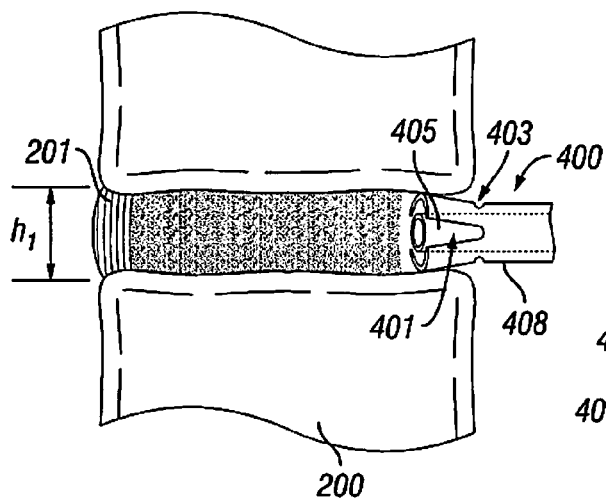
FIG. 13A shows the bone tamp of FIG. 10 in an expanded configuration.
Figure 13B:
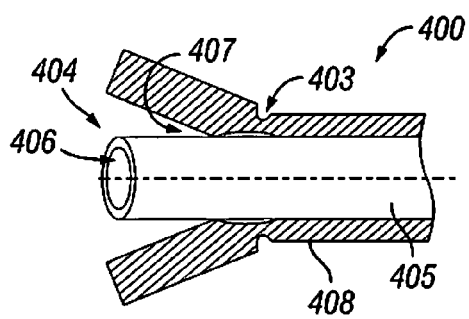
FIG. 13B shows a detail cross section view of the expanded bone tamp of FIG. 12A.

FIG. 13A shows the bone tamp 400 in an expanded configuration, and FIG. 13B shows a detail view of the expanded bone tamp 400 of FIG. 13A. The outer tube 408 may be expanded by advancing the inner cannula 405 toward the distal opening 404. Since the cannula 405 is wider than the narrowed inner diameter 407 of the distal end, the advancement of the cannula 405 forces the distal end to expand along axial cuts 401. Circumferential cuts 403 and opening 402 may aid the expansion by creating a hinge-like section of the outer tube 408. In particular, cuts 403 may collapse or be compressed to accept the dimensional changes that accompany expansion of the outer tube 408, as shown in FIG. 13B. Cannula 405 may be advanced through the bone tamp 400 by means of threads, a screw-like mechanism, an auger-like mechanism, a lever, or any other appropriate means, as will be understood by one skilled in the art of medical devices.

Figure 14A:
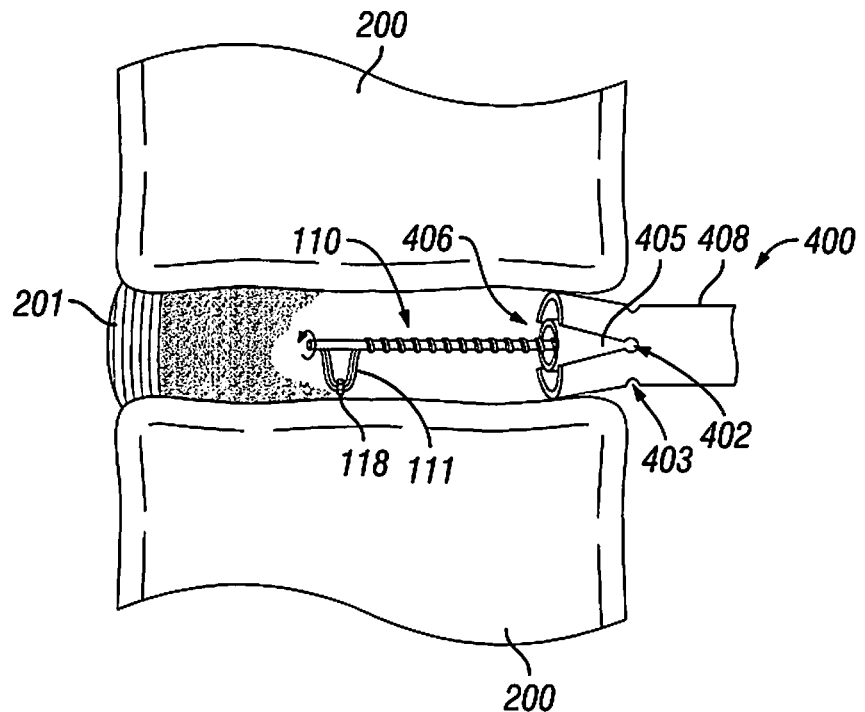
FIG. 14A shows the bone tamp of FIG. 10 used in conjunction with a power tool.
Figure 14B:
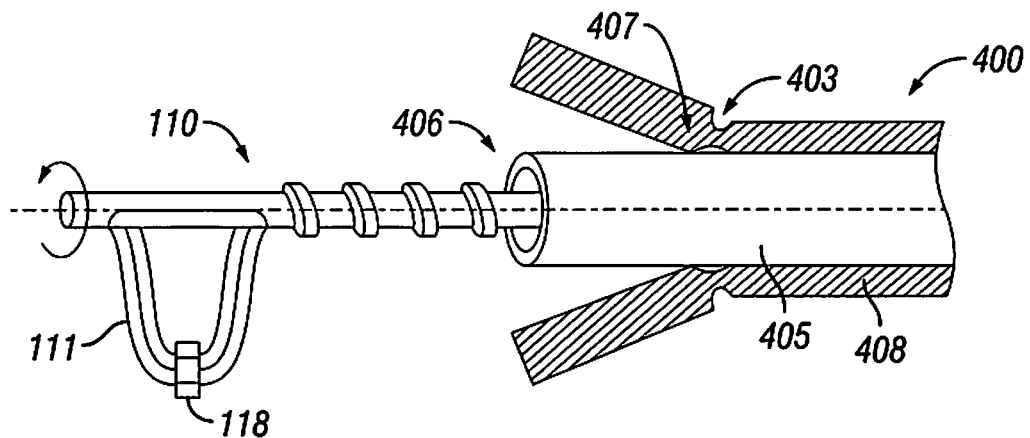
FIG. 14B shows a detail partial cross section view of the bone tamp and power tool of FIG. 13A.

FIG. 14A shows a bone tamp 400 used in conjunction with a power tool 100, and FIG. 14B shows a detail view of the bone tamp 400 and power tool shaft 110 of FIG. 14A. Cannula 405 provides a clear passage for a straight instrument to be inserted between the vertebrae 200 following expansion by the outer tube 408. One example of such an instrument is the shaft 110 of power tool 100. FIG. 14A shows a shaft 110 inserted through the cannula 405, exiting at the cannula's distal port 406 and operating on the intervertebral disc 201. The bone tamp 400 may provide a minimal operating height, or more, between the vertebrae 200 for the cutting element 111 to operate. If the distance is greater than the minimum needed by the cutting element, the cutting height of the cutting element 111 may be adjusted by the surgeon or user, as described above with respect to power tool 100. A surgeon or operator may monitor the removal of tissue and the overall discectomy using arthroscopic or endoscopic techniques or any other appropriate means, as will be understood by one skilled in the art of minimally invasive surgery.

While automated tools, such as the power tool 100 described above, are superior to manual tools in many situations, there are nonetheless circumstances that call for the use of manual tools. For example, a manual tool may be necessary for creating an initial cavity for a bone tamp or power tool. Many manual tools, however, do not have a shape that is compatible with either the inflatable bone tamp or expanding bone tamp described above. These tools may have shapes with protrusions or other features that would prevent the tool from passing through the inner lumen of the bone tamps. One solution to this problem is to provide an expanding manual tool that can change its shape once it passes through the lumen to the site of surgery.

Figure 15A:
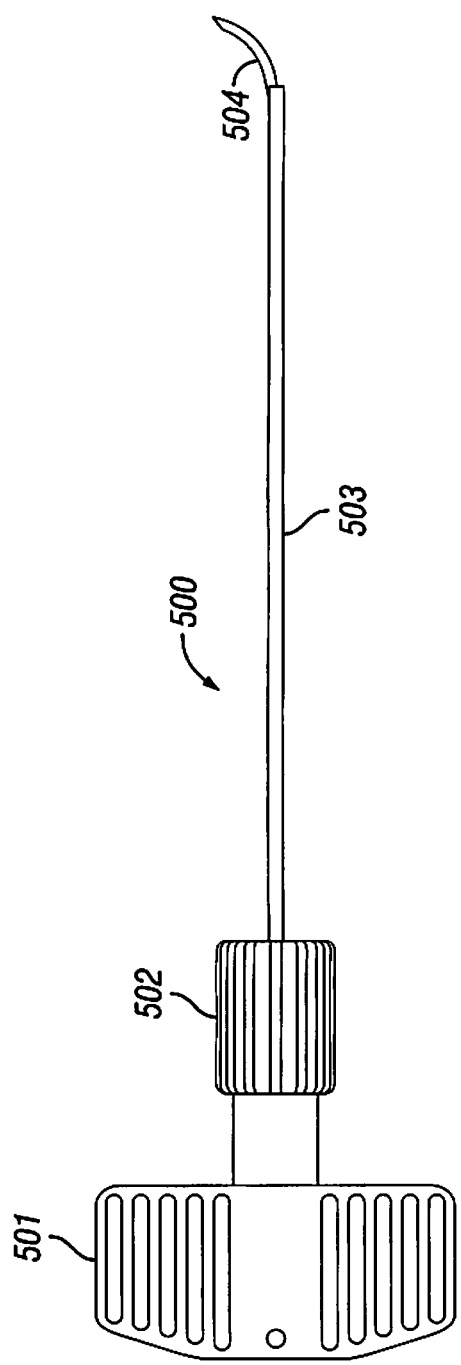
FIG. 15A shows an expanding scraper that may pass through the lumen of a bone tamp, according to an aspect of the disclosure.
Figure 15B:
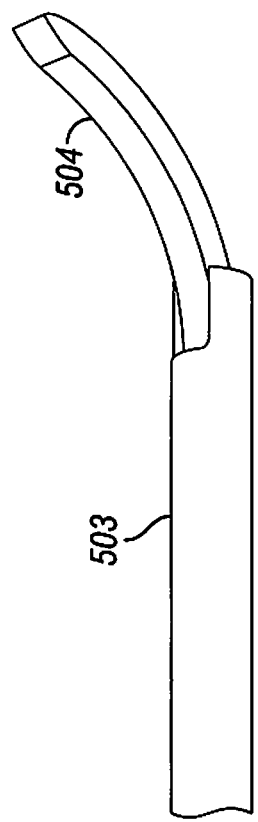
FIG. 15B shows the expanding scraper of FIG. 14A with the tip extended.

FIG. 15A shows an expanding scraper 500 that may pass through the lumen of a bone tamp, according to an aspect of the disclosure. The scraper may include a T-handle 501, a rotating control knob 502, a shaft 503, and a tip 504. Twisting the knob 502 may cause extension or retraction of curved tip 504 through a threaded mechanical connection between knob 502 and shaft 503. FIG. 15B shows the expanding scraper 500 with the tip 504 extended.

Figure 16:
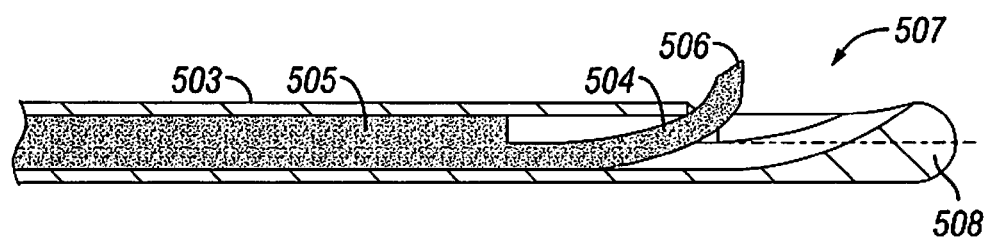
FIG. 16 shows a cutaway view of the expanding scraper of FIG. 14A with the tip in a partially retracted position.
Figure 17:
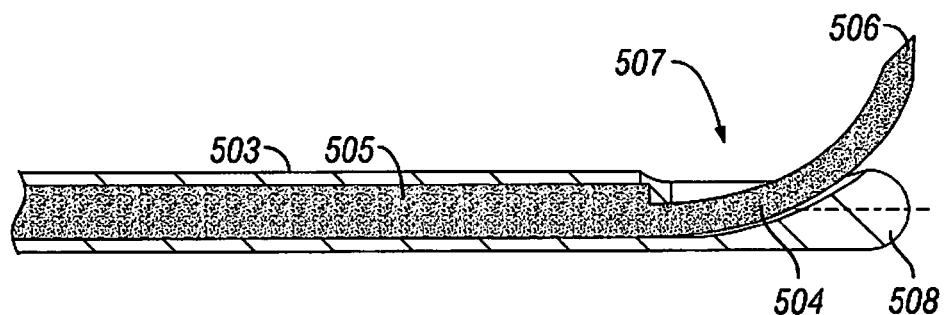
FIG. 17 shows a cutaway view of the expanding scraper of FIG. 14A with the tip in an extended position.

FIG. 16 shows a cutaway view of the expanding scraper 500 with the tip 504 in a retracted position, and FIG. 17 shows a cutaway view of the expanding scraper with the tip 504 in an extended position. Inner core 505 may be fixed to the handle 501. Outer shaft 503 may surround the inner core 505 and may provide a window 507 for the extension of the tip 504. Twisting the control knob 502 may draw the outer shaft 503 along the inner core 505. Twisting knob 502 in one direction may cause the shaft 503 to retract and expose the tip 504, while twisting knob 502 in the opposite direction may cause shaft 503 to extend and withdraw the tip 504. The outer shaft 503 may be keyed to the handle 501 so that when the handle 501 is rotated, the shaft 503 does not rotate relative to the inner core 505. The mechanical connection between shaft 503 and knob 502 may take the form of threads or the like.

The inner core 505 may be made of a superelastic metal, such as, e.g., nitinol. The tip 504 may include a sharp point 506, as well as sharp edges, to facilitate cutting through both soft tissue, such as the intervertebral disc, and cancellous bone. The distal end of the outer shaft 503 may be a domed closure 508.

While the disclosure has been described in terms of exemplary aspects, those skilled in the art will recognize that the disclosure can be practiced with modifications in the spirit and scope of the appended claims. These examples given above are merely illustrative and are not meant to be an exhaustive list of all possible designs, aspects, applications or modifications of the disclosure.

What is claimed is:

1. A device for the removal of an intervertebral disc or a portion thereof, the device comprising:
    an outer portion configured to be manipulated by a user of the device;
    an outer sheath connected to the outer portion, wherein the outer sheath comprises a proximal end and a distal end, the distal end of the outer sheath located generally proximate to a flexible cutting element;
    an inner core connected to the outer portion and extending through the outer sheath, the inner core comprising the flexible cutting element located distal to a distal end of the outer sheath, wherein the distal end of the outer sheath is closer to the flexible cutting element than the proximal end of the outer sheath;
    an auger portion surrounding the inner core configured to remove tissue and bone material that has been cut by the flexible cutting element, the auger portion located between the cutting element and the proximal end of the outer sheath;
    a spring and a plunger provided within the outer sheath, wherein the inner core is connected to the plunger, wherein the spring is configured to press against the plunger to decrease a height of the flexible cutting element, wherein the spring is positioned distally to the plunger such that it is closer to the distal end of the outer sheath than the plunger;
    a motor configured to rotate the inner core;
    a trigger configured to adjust the height of the flexible cutting element;
    the trigger connected to the plunger, whereby rotation of the trigger causes the plunger to move distally; and
    a connector connecting the plunger to the motor such that when a distance between the plunger and the motor varies, the plunger is not disconnected from the motor;
    an outer core connected to the inner core and located between the inner core and the outer sheath, the outer core comprising the auger portion located between the outer sheath and the flexible cutting element,
    wherein the auger portion helically surrounds the inner core, the auger portion configured to rotate to remove tissue and bone material that has been cut by the flexible cutting element at the distal end of the outer sheath and move the tissue and bone material to the proximal end of the outer sheath.

2. The device of claim 1, wherein the outer core is configured to be rotated by one of the motor or the inner core.

3. The device of claim 1, wherein the flexible cutting element comprises a metal, a superelastic metal, or a polymer.

4. The device of claim 1, wherein the flexible cutting element comprises a braided cable, a linked chain, a dual blade, or a flexible member.

5. The device of claim 1, wherein the trigger is configured to be squeezed by a user of the device.

6. The device of claim 1, further comprising at least one battery configured to provide power to the motor.

7. The device of claim 1, wherein the flexible cutting element is adjustable to a height between 0 mm and 20 mm.

8. The device of claim 7, wherein the flexible cutting element is adjustable to a height between 4 mm and 16 mm.

9. A system for separating two vertebrae that are in close proximity, the system comprising:
    a balloon comprising a collapsed state, an expanded state, a proximal end, and a distal end, the balloon configured to be inserted between adjacent vertebrae;
    a central shaft comprising a proximal end and a distal end, the central shaft connected at its distal end to the proximal end of the balloon, the central shaft in fluid communication with the balloon;
    an inflation port in fluid communication with the central shaft, the inflation port configured to transport a fluid to and from the balloon to transition the balloon between a collapsed state and an expanded state;
    an inner lumen located within the central shaft but sealed against fluid communication with the central shaft, balloon, and inflation port, the inner lumen passing through the balloon to a distal port on the distal end of the balloon;
    a lumen port located at the proximal end of the central shaft, the lumen port connected to the inner lumen, wherein the lumen port, inner lumen, and distal port define a linear path from the proximal end of the central shaft to the distal end of the balloon; and a power tool inserted into the lumen port, wherein the power tool comprises:

an outer sheath comprising a proximal end and a distal end, the distal end of the outer sheath located generally proximate to a cutting element;

an inner core extending through the outer sheath, the inner core comprising the cutting element, wherein the distal end of the outer sheath is closer to the cutting element than the proximal end of the outer sheath;

an auger portion surrounding the inner core configured to remove tissue and bone material that has been cut by the cutting element, the auger portion located between the cutting element and the proximal end of the outer sheath;

a spring and a plunger provided within the outer sheath, wherein the spring is positioned distally to the plunger such that it is closer to the distal end of the inner core comprising the cutting element than the plunger;

a motor configured to rotate the inner core;

a trigger configured to adjust the height of the cutting element, wherein the trigger is connected to the plunger, whereby rotation of the trigger causes the plunger to move distally; and a connector connecting the plunger to the motor such that when a distance between the plunger and the motor varies, the plunger is not disconnected from the motor;

an outer core connected to the inner core and located between the inner core and the outer sheath, the outer core comprising the auger portion located between the outer sheath and the flexible cutting element, wherein the auger portion helically surrounds the inner core, the auger portion configured to rotate to remove tissue and bone material that has been cut by the flexible cutting element at the distal end of the outer sheath and move the tissue and bone material to the proximal end of the outer sheath.

10. The system of claim 9, wherein the fluid comprises at least one of air, saline, or nitrogen gas.

11. A device for the removal of bone or tissue, the device comprising:

a handle;

an outer shaft connected to the handle, the outer shaft comprising a rounded tip distal to the handle and a window on one side of the shaft near the rounded tip;

an inner core located in the outer shaft and connected to the handle, the inner core comprising a curved tip configured to cut through bone or tissue, wherein the inner core includes a proximal end and a distal end, wherein the proximal end is closer to the handle than the distal end;

an auger portion surrounding the inner core configured to remove the bone or tissue that has been cut by the curved tip, the auger portion located between the curved tip and the handle;

a spring and a plunger provided within the outer shaft, wherein the inner core is connected to the plunger, wherein the spring is configured to press against the plunger to decrease a height of a flexible cutting element, wherein the spring is positioned distally to the plunger such that it is closer to the distal end of the inner core comprising the curved tip than the plunger;

a knob connected to the handle and to the outer shaft, the knob configured to slide the outer shaft relative to the inner core, thereby extending and retracting the curved tip through the window in the outer shaft;

a trigger connected to the plunger, whereby rotation of the trigger causes the plunger to move distally; and a connector connecting the plunger to the motor such that when a distance between the plunger and the motor varies, the plunger is not disconnected from the motor, an outer core connected to the inner core and located between the inner core and an outer sheath having a proximal end and a distal end, the distal end of the outer sheath located generally proximate to the flexible cutting element, the outer core comprising the auger portion located between the outer sheath and the flexible cutting element;

wherein the auger portion helically surrounds the inner core, the auger portion configured to rotate to remove tissue and bone material that has been cut by the flexible cutting element at the distal end of the outer sheath and move the tissue and bone material to the proximal end of the outer sheath.

12. The device of claim 11, wherein the outer shaft is configured to be rotationally stationary relative to the handle.

13. The device of claim 11, wherein the handle is a T-handle.

14. The device of claim 11, wherein the inner core comprises a superelastic metal.

15. The device of claim 14, wherein the superelastic metal is nitinol.

16. The device of claim 11, wherein the curved tip comprises a sharp point and sharp edges configured to cut through bone or tissue.

* * * * *